(12) United States Patent
Tuke et al.

(10) Patent No.: US 7,497,876 B2
(45) Date of Patent: Mar. 3, 2009

(54) PROSTHETIC IMPLANT

(75) Inventors: Michael A. Tuke, Guildford (GB);
Andrew C. Taylor, Nr Chichester (GB);
Peter Thomsen, Vastra Frölunda (SE);
Mark Taylor, Loughborough (GB)

(73) Assignee: Finsbury (Development) Limited,
Leatherhead (GB)

( * ) Notice: Subject to any disclaimer, the term of this patent is extended or adjusted under 35 U.S.C. 154(b) by 459 days.

(21) Appl. No.: 10/979,513

(22) Filed: Nov. 2, 2004

(65) Prior Publication Data
US 2005/0119759 A1 Jun. 2, 2005

(30) Foreign Application Priority Data
Nov. 3, 2003 (GB) ................................. 0325647.6

(51) Int. Cl.
*A61F 2/28* (2006.01)
*A61F 2/36* (2006.01)

(52) U.S. Cl. ............... 623/23.5; 623/23.55; 623/23.29; 623/16.11

(58) Field of Classification Search ... 623/23.29–23.31, 623/16.11, 23.5–23.55, 23.72–23.76, 22.31, 623/22.33; 264/21, 400–402
See application file for complete search history.

(56) References Cited

U.S. PATENT DOCUMENTS

| 3,905,777 | A | | 9/1975 | Lacroix | |
|---|---|---|---|---|---|
| 4,608,053 | A | * | 8/1986 | Keller | 623/23.31 |
| 4,673,409 | A | * | 6/1987 | Van Kampen | 623/23.29 |
| 4,851,008 | A | * | 7/1989 | Johnson | 623/23.5 |
| 5,108,435 | A | * | 4/1992 | Gustavson et al. | 623/23.53 |
| 5,192,324 | A | * | 3/1993 | Kenna | 623/23.55 |
| 5,496,372 | A | * | 3/1996 | Hamamoto et al. | 623/23.54 |
| 5,507,815 | A | * | 4/1996 | Wagner et al. | 623/23.5 |
| 5,645,740 | A | * | 7/1997 | Naiman et al. | 219/121.68 |
| 5,910,173 | A | * | 6/1999 | DeCarlo et al. | 128/898 |

(Continued)

FOREIGN PATENT DOCUMENTS

EP 0 552 950 A1 7/1993

(Continued)

OTHER PUBLICATIONS

European Patent Office, European Search Report for Application No. EP 04 25 6694, Mar. 1, 2005, 5 pp., Munich, Germany.

*Primary Examiner*—Alvin J Stewart
(74) *Attorney, Agent, or Firm*—Senniger Powers LLP

(57) ABSTRACT

The invention relates to an element for incorporation into a prosthetic implant so as to form a bone-contacting portion thereof, the element comprising a rear face, a front face, and a body extending between the rear face and the front face, wherein the front face comprises a basal surface and at least one upstanding portion projecting above the basal surface and having a transverse hole extending therethrough from one side of the upstanding portion to another. It further relates to a prosthetic implant for implantation into a patient so as to contact a bone of the patient, the prosthetic implant comprising a body including a bone-contacting portion for contacting the patient's bone after implantation of the prosthetic implant, wherein the bone-contacting portion is provided with at least one upstanding portion that projects above a surrounding basal surface portion and that is provided with a transverse hole that extends through the upstanding portion from one side to another.

28 Claims, 4 Drawing Sheets

U.S. PATENT DOCUMENTS

| | | | | |
|---|---|---|---|---|
| 6,129,884 | A * | 10/2000 | Beers et al. | 264/401 |
| 6,149,689 | A * | 11/2000 | Grundei | 623/23.5 |
| 6,193,762 | B1 * | 2/2001 | Wagner et al. | 623/66.1 |
| 6,519,500 | B1 * | 2/2003 | White | 700/119 |
| 7,122,057 | B2 * | 10/2006 | Beam et al. | 623/23.51 |
| 7,208,222 | B2 * | 4/2007 | Rolfe et al. | 428/304.4 |
| 7,214,246 | B2 * | 5/2007 | Serbousek et al. | 623/23.31 |
| 7,244,275 | B2 * | 7/2007 | Michelson | 623/23.5 |
| 2001/0053937 | A1 * | 12/2001 | Johnson et al. | 623/23.34 |
| 2003/0065400 | A1 * | 4/2003 | Beam et al. | 623/23.51 |
| 2005/0119759 | A1 * | 6/2005 | Tuke et al. | 623/23.49 |
| 2008/0021586 | A1 * | 1/2008 | Schillen et al. | 700/120 |
| 2008/0050524 | A1 * | 2/2008 | Kumar et al. | 427/289 |
| 2008/0124663 | A1 * | 5/2008 | Anderson et al. | 430/324 |
| 2008/0195232 | A1 * | 8/2008 | Carr-Brendel et al. | 623/23.76 |
| 2008/0212266 | A1 * | 9/2008 | White | 361/679 |
| 2008/0233343 | A1 * | 9/2008 | Cheng et al. | 428/114 |

FOREIGN PATENT DOCUMENTS

| | | |
|---|---|---|
| EP | 0 668 062 A1 | 8/1995 |
| FR | 2 548 889 A1 | 1/1985 |

* cited by examiner

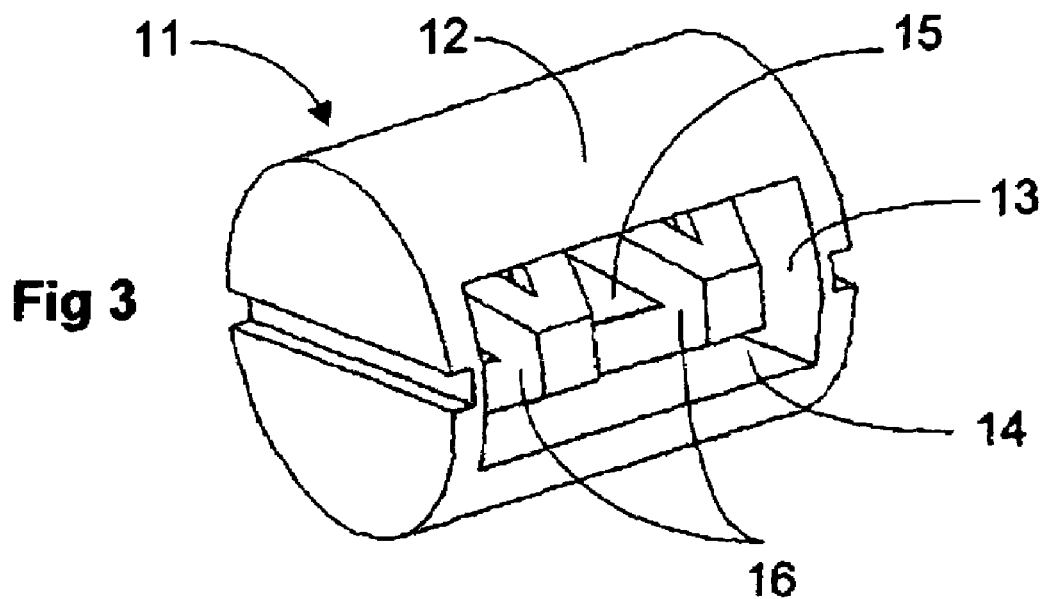
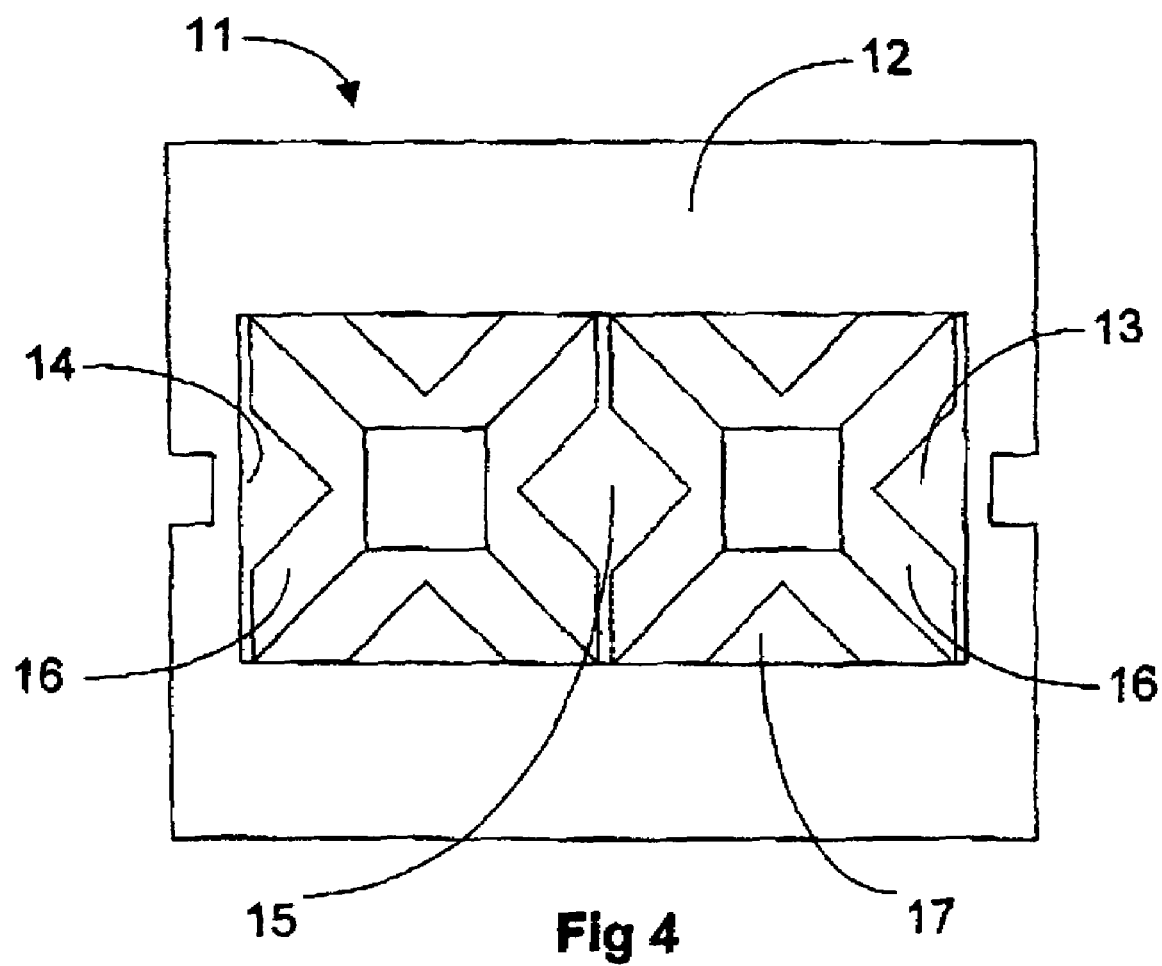

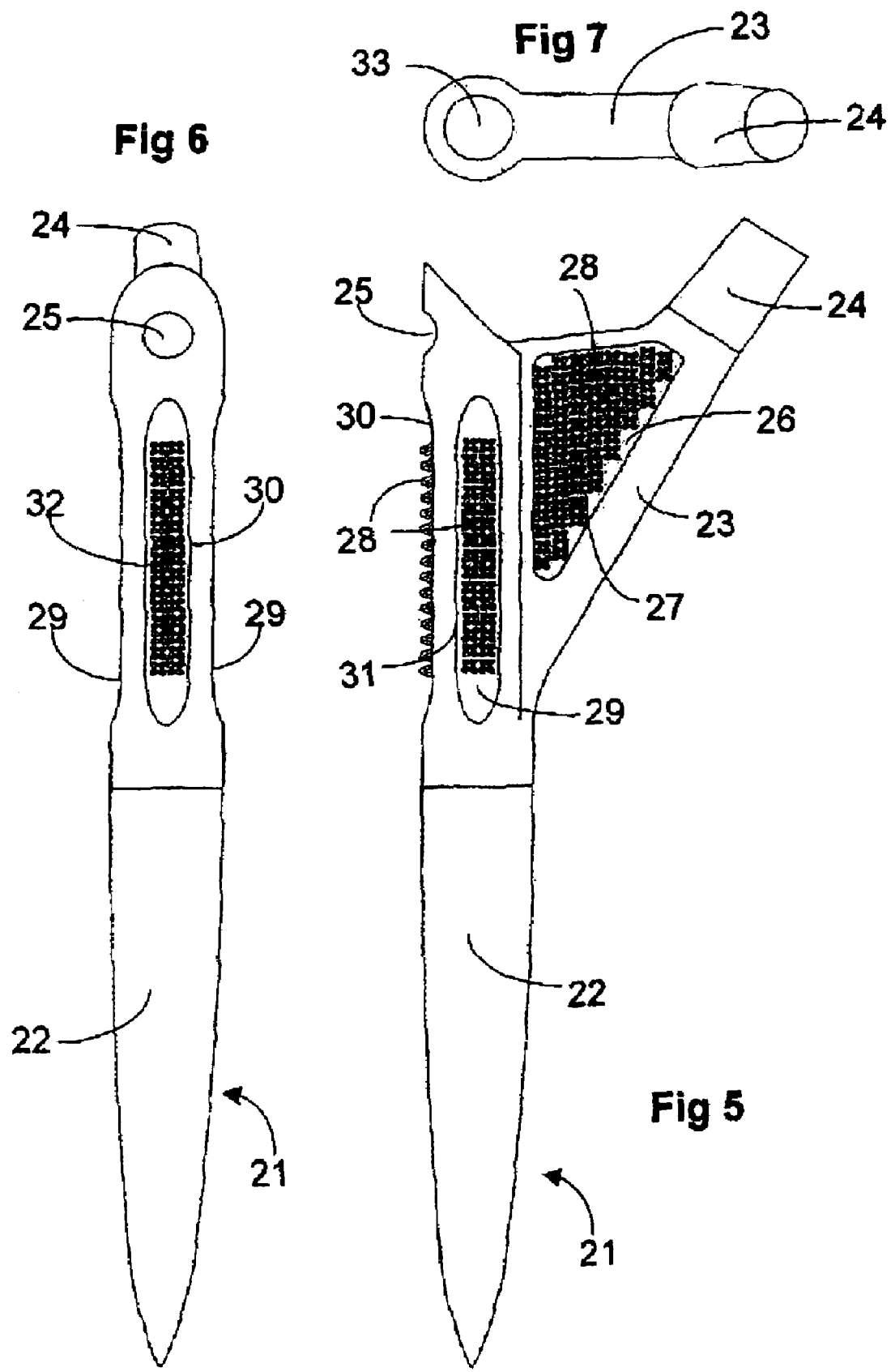

PROSTHETIC IMPLANT

This invention relates to a prosthetic implant, more particularly to a prosthetic implant for implantation in or on a bone of a patient, and to an element for incorporation in such a prosthetic implant.

The use of prosthetic implants for surgical implantation in or on a bone of a patient is long established. Thus, in the case of a damaged or diseased hip joint, implantation of a prosthetic femoral implant, a prosthetic acetabular implant, or both, is a common surgical procedure. Another operation frequently performed by orthopaedic surgeons is knee replacement, in which a tibial implant is inserted in the top of a patient's tibia, while one or both condylar surfaces of the patient's femur may be replaced at the same by corresponding femoral implants. In case of accidental fracture of long bones bone plates may be used to stabilise and strengthen the bones. Shoulder, fig, ankle, and elbow replacement prostheses are also known.

In all of these surgical procedures the prosthetic implant is intended to bear load. Thus the objective is to fix the prosthetic implant into or onto the bone into or onto which it is implanted as firmly as possible and so as to maintain the bone under loading conditions which are as near as possible to those prevailing the undamaged bone. This is because living bone tissue, which is continually being dissolved and redeposited by the body, tends to disappear unless it is maintained under the appropriate loading level.

While bone cement is frequently used to affix a prosthetic implant to the bone, it is generally recognised that, if possible, it is better to avoid the use of bone cement. One benefit of avoiding the use of bone cement is that there is a greater opportunity for the implant to form a bond with the surrounding bone. Hence a considerable effort has been made to develop prosthetic implants having surface finishes which are intended to promote bone ingrowth and bonding to the implant. To this end the bone-contacting portions of many prosthetic implants which are to be used without bone cement are provided with a surface coating of hydroxyapatite with a view to promoting bonding of bone to the prosthetic implant.

It is well known that the life expectancy of a prosthetic implant is largely influenced by fatigue fracture and wear. In particular, torsion, shear and bending stresses acing through the prosthetic implant can result in the weakening of the interface between the prosthetic implant and the bone, especially when cement is used to bond the prosthetic implant to the bone. If such weakening occurs, then wear is inevitable, and this can lead to particle formation which causes osteolysis and adverse tissue reactions. These factors not only reduce the life expectancy of a prosthetic implant but can cause considerable damage to the bone of the patient.

The average lifespan of conventional prosthetic implants is about 15 years. Therefore, if a prosthetic implant is to be implanted into an elderly patient, such a working life span is not problematic as the prosthetic implant might reasonably be expected to function for the remaining lifetime of the patient. However, when such a prosthetic implant is implanted into a young patient, it is likely that one or more revision operations will have to be performed during the lifetime of the patient. It is highly undesirable to subject patients repeatedly to the trauma of such a major surgical procedure as is required to replace a failed prosthetic implant.

It is recognised that the life expectancy of a prosthetic implant might be improved by providing the surface of the implant with features promoting bone ingrowth.

GB-A-2182354 discloses an orthopaedic implant having a surface which, in use, is intended to contact bone and which has a finely patterned conformation composed of a plurality of raised portions separated from each other by indented portions, the indented portions being of a width and depth to allow bone penetration which in use promote an interference fit between the implant and adjacent bone in the region of the patterned area.

EP-A-1133957 teaches a prosthetic implant having an anchoring surface provided with a plurality of channels which, when the implant is in position, permits bone ingrowth. Each channel has an opening on the anchoring surface and an undercut region interior of the anchoring surface. Typically the opening is at least 50 µm across. One technique for producing such channels is wire electrodischarge machining. However, forming such channels with undercut regions via the methods suggested is time consuming, and adds additional expense to the production cost of such prosthetics.

U.S. Pat. No. 5,676,700 describes structural elements having a shape similar to caltrops which are designed to interlock with one another in an array to repair, augment or replace natural bone.

There is a need in the art to provide an improved form of prosthetic implant which is better able to bear stress and which minimises wear at the bone-prosthetic implant interface, thus maximising the life expectancy of the prosthetic implant and reducing the likelihood of further surgery for replacement or repair being required.

The present invention seeks to prepare an improved prosthetic implant capable of providing in use a strong cementless fixation to an adjacent bone, wherein bone ingrowth can occur into porous structures on the surface of the prosthetic implant.

According to a first aspect of the present invention there is provided an element for incorporation into a prosthetic implant so as to form a bone-contacting portion thereof, the element comprising a rear face, a front face, and a body extending between the rear face and the front face, wherein the front face comprises a basal surface and at least one upstanding portion projecting above the basal surface and having at least one transverse hole extending therethrough from one side of the upstanding portion to another.

The height of the upstanding projection above the basal surface is typically less than about 2 mm, for example from about 0.75 to about 1.75 mm.

Preferably the at least one transverse hole has an axis which extends substantially parallel to the basal surface.

The upstanding portion may be of any suitable configuration. Where there is more than one upstanding portion projecting above the basal surface they may be of the same or different configuration.

The upstanding portion may be of substantially an arched configuration. The arch may be of a generally curved profile or may be of a triangular or square profile. Thus the arch may be an inverted U or V. In an alternative arrangement, the upstanding portion may have a plurality of arches and therefore may be, for example, an inverted W.

Preferably the upstanding portion has a footprint on the basal surface in the shape of a regular polygon having up to about 8 sides or it may have a circular or elliptical footprint on the basal surface. For example, the upstanding portion may substantially comprise a truncated pyramid. Thus the upstanding portion may substantially comprise a truncated rectangular pyramid, for example a truncated square pyramid. In this arrangement the upstanding portion may be provided with first and second holes each of which extends from a respective first face to a respective second face opposite the corresponding first face. The two holes may intersect substantially at right angles. Thus the finished upstanding portion may be four slopped legs conjoined at their upper end.

Alternatively the upstanding portion can substantially comprise a truncated triangular pyramid. In this case the upstanding portion can have a first hole which extends from a first face, which bends in the interior of the upstanding portion, and which extends to a second face of the upstanding portion, as well as a further hole which extends from a third face to intersect the first hole.

Another possibility is for the upstanding portion to substantially comprise a truncated hexangular pyramid. In this case the upstanding portion can be provided with first, second and third holes, each of which extends from a respective first face to a restive second face opposite the corresponding first face. These first, second and third holes may intersect.

The ratio of the greatest transverse dimension of the upstanding portion (i.e. the length measured along a diagonal line for a truncated square pyramid or the diameter for a circular upstanding portion) to its height measured above the immediately surrounding basal surface typically ranges from about 0.5:1 to about 3.0:1, but is preferably in the range of from about 0.75: to about 2.0:1, e.g. about 1:1.

The at least one upstanding portion may generally have a rough surface to further bone ingrowth. "Rough" means not polished.

If desired, the upstanding portions can be provided with a head portion that enhances interlocking with the bone as a result of bony ingrowth. For example, they can be provided with enlarged ball heads.

It may be preferred that the basal surface is surrounded by a raised rim. The height of the raised rim above the basal surface may be less than, more than, or substantially the same as, the height of the upstanding portions above the basal surface. The raised rim may surround two or more upstanding portions so that the upper surfaces of the upstanding portions and the rim together define an outer envelope for at least a part of the bone-contacting portion of the prosthetic implant, and so that the basal surfaces comprise valleys within a corresponding rim. In a preferred arrangement each element will include two upstanding portions surrounded by the rim.

Conveniently the, or each, element is substantially rectangular in plan. Alternatively the element has the form of a sleeve, in which case the rear face comprises the inner face of the sleeve and the from face comprises the outer face of the sleeve. The element may be of any suitable size. In one arrangement it may have the dimensions of about 2 mm by about 4 mm.

The invention further provides a prosthetic implant having a body and at least one element of the above first aspect connected at the rear ce to the body. Thus the front face of the element provides a bone-contact surface on the element. The at least one element may be preformed and secured to the body by any suitable means. In one arrangement, the at least one element is bonded to the body of the implant. The at least one element may be bonded by means of hot isostatic pressing (HIPing). In one alternative arrangement the at least one element can be secured to the prosthetic implant by means of screws, bolts or cement.

In an alternative arrangement, the upstanding portions can be integrally formed with the femoral implant.

The prosthetic implant of the present invention may be any prosthesis and may be a femoral hip prosthesis, an acetabular hip prosthesis, a shoulder prosthesis, a knee prosthesis, a finger prosthesis, an ankle prosthesis, or a bone plate. In one preferred embodiment the prosthetic implant is a femoral implant, and the bone-contacting portion of the prosthetic implant comprises a stem of the implant for insertion in a surgically prepared channel in a resected upper end of a femur of the patient. In this case the element may have the form of a sleeve bonded to the stem.

The prosthetic implant may be a femoral implant having a stem for insertion in a surgically prepared channel in a resected upper end of a femur of the patient, a wedge-shaped portion having a front face and a rear face extending laterally from an upper end of the stem and a spigot for receipt of a ball head on the wedge-shaped portion, the ball head being for insertion in a natural or artificial acetabular socket, while the bone-contacting portion of the prosthetic implant comprises at least a portion of at least one out of the front and rear faces of the wedge-shaped portion.

In an alternative arrangement, the prosthetic implant can be a femoral implant having a stem for insertion in a surgically prepared channel in a resected upper end of a femur of the patient, a wedge-shaped portion having a front face and a rear face extending laterally from an upper end of the stem, and a ball head on the wedge-shaped portion, the ball head being adapted for insertion in a natural or artificial acetabular socket, and the bone-contacting portion of the prosthetic implant can comprise at least a portion of at least one out of the front and rear faces of the wedge-shaped portion.

The element of the above first aspect and/or the implant of the above second aspect may be made from any suitable material. Suitable materials include stainless steel, cobalt-chrome or titanium. Although not generally preferred, the element and/or the implant may be coated with material to promote bone growth such as hydroxyapatite.

Compared with prosthetic implants, such as those of GB-A-2182354, the prosthetic implant of the present invention has the advantage that the bone can penetrate the holes in the upstanding portions and truly lock the bone and implant together. In comparison to the prosthetic implants of EP-A-1133957, which have channels for bone ingrowth but no means for preventing lateral movement between the bone and channel in the direction of the length of the channel, the prosthetic implants of the present invention possess the advantage that, after bone ingrowth through the holes in the upstanding portions has occurred, the bone and prosthetic implant are securely locked one to another with no possibility of relative movement. In addition, in some arrangements the methods used for making the elements and prosthetic implants of the present invention may permit more cost-effective fabrication than the methods proposed in EP-A-1133957.

The at least one upstanding portion may be formed by any suitable means. However, due to the small size casting will generally not be used. In one arrangement the at least one upstanding portion may be formed either separately or directly on the basal surface by selective laser beam melting, selective electron beam melting or selective sintering with selective electron beam melting being particularly preferred. The whole element may be formed surface by selective laser beam melting selective electron beam melting or selective sintering with selective electron beam melting being particularly preferred.

Selective laser melting is a two-dimensional production process resulting in a three dimensional solid object. It enables production of components from three-dimensional stereolithography computer assisted drawing (CAD) data. The direct laser melting process entails spreading, optionally using a roller mechanism, a thin layer of a metal powder across an area on a metal substrate where an upstanding portion is to be built. A typical metal powder has a particle size of about 20 µm. A cross section of the upstanding portion is then selectively "drawn" on the layer of powder using energy from a laser, such as a $CO_2$ laser. The laser fuses the metal powder so as to form a first layer of the eventual upstanding portion. This sequence of operations is then repeated as often as required until the desired shape of the upstanding portion has been created. An offset technique allows, for example bridges to be formed.

One advantage of the use of such a process is that, by changing the intensity of the laser beam at the edges of each layer of the upstanding portion, the result is that the outer surface of the upstanding portion is rendered semi-diffused, thus resulting in a porous outer micro-structural layer. This layer facilitates impregnation of a coating, such as a crystalline form of hydroxyapatite, which can thus promote osteointegration after implantation.

Electron beam melting is a similar procedure except that an electron beam is used instead of a laser to effect fusion of the metal powder. The electron beam is focused using a series of electromagnets in a similar manner to that used to control the electron beam in a conventional television set. As with the laser melting process the intensity of the electron beam can be varied at the edges of each layer of the upstanding portions.

Selective laser sintering is another process that can be used to build up an upstanding portion on a substrate. In this case a polymer-coated metal powder is used. A laser beam is used to "draw" the desired layer outline and results in fusion of the polymer in the area which has been illuminated by the laser beam. As with laser melting and electron beam melting processes the upstanding portion is built up from many layers. Subsequent sintering and hipping of the layers results in pyrolysis of the polymer binder and sintering of the resulting preforms produces a dense metallic structure.

These processes can be used to produce elements according to the invention on the surface of implants or as performs for subsequent bonding to a prosthetic implant by a procedure such as hot isostatic pressing or diffusion bonding. The direct laser melting and electron beam melting processes enable production of an element in the form of a tile having a front face upon which are formed one or more upstanding portions of the desired shape and a rear face by which the tile can be bonded to a prosthetic implant. Several such tiles can be bonded or otherwise secured to the same prosthetic implant as desired. Thus for example, one or more tiles produced by one of these processes can be bonded to the front and/or rear face of a wedge-shaped portion of a femoral prosthetic implant which projects laterally firm the stem of the implant and has a ball head at its laterally outer end for reception in a natural or artificial acetabular cup. On the other hand, the selective laser sintering process enables the production of an element in the form of a sleeve which can subsequently be bonded to a prosthetic implant, for example to the stem of a femoral prosthetic implant.

Other methods of securing such tiles or sleeves to prosthetic implants include use of screws, bolts, or cement.

According to a further aspect of the present invention there is provided a test element for use in animal testing having at least one upstanding portion projecting from both an obverse and a reverse face of a bas surface. Each face of the test element may have the features of the element of the above-first aspect. In general in testing prosthesis in animals such as rabbits, 12 rabbits will generally be required for each test to deal with different sizes, and propensity to carry out activity varies. Thus if a coating is being compared with an uncoated arrangement, 24 rabbits will be required. However, with the test element of the present invention, one face of the element can be coated and the other un-coated. Thus the coated and uncoated arrangement can be tested in the same animal. Thus the number of animals having to be used will be substantially reduced.

In order that the invention may be clearly understood and readily carried into effect, a preferred embodiment thereof will now be described, by way of example only, with reference to the accompanying drawings wherein;

FIG. 3 is a perspective view of a second form of test implant;

FIG. 4 is a side view of the test implant of FIG. 3;

FIG. 5 is a front view of a femoral implant in accordance with the invention;

FIG. 6 is a side view of the femoral implant of FIG. 5;

FIG. 7 is a top plan view of the femoral implant of FIGS. 5 and 6; and

Figure 1:
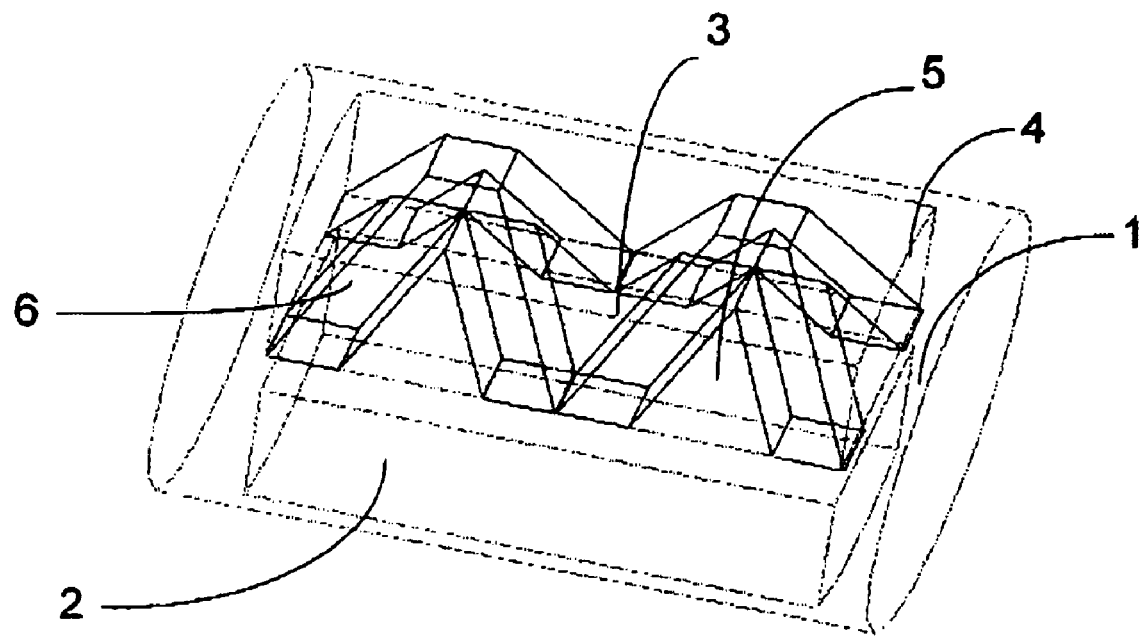
FIG. 1 is an enlarged perspective view of a test implant for evaluating bone ingrowth after implantation into a rabbit's femur.
Figure 2:
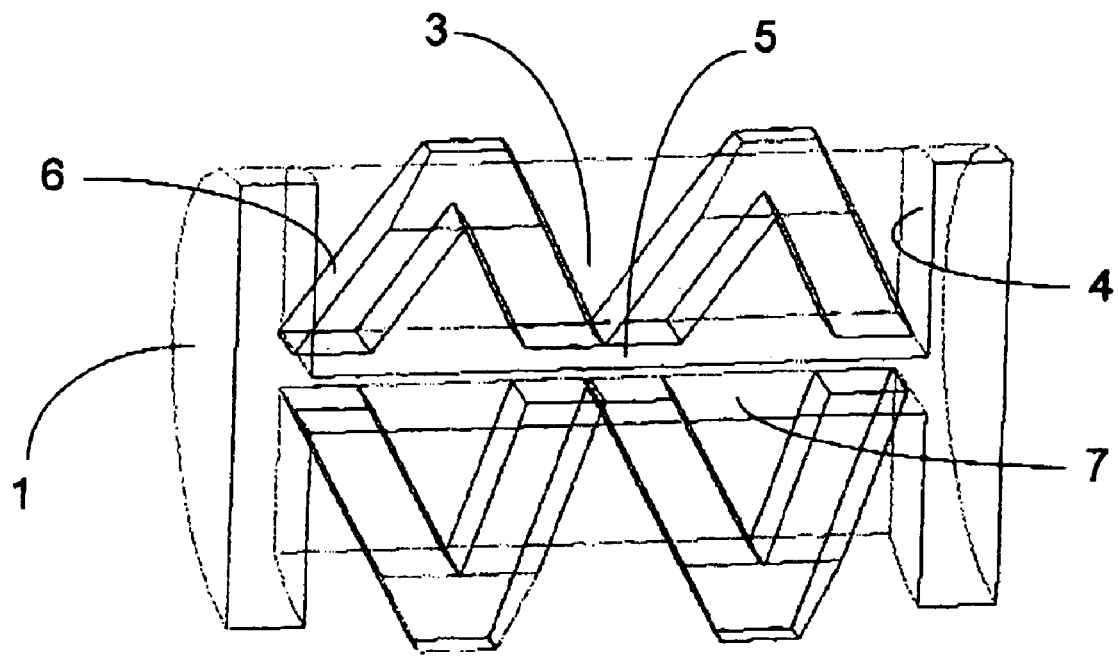
FIG. 2 is a cross section of the test implant of FIG. 1.

Referring to FIGS. 1 and 2 of the drawings, a test implant 1 has an outer surface 2 which forms part of a substantially cylindrical envelope. It is of generally rectangular configuration i.e. it has a rectangular footprint. The implant 1 has opposed recesses 3 which are substantially rectangular in shape and which are surrounded by walls 4. Recesses 3 each have a basal surface 5 on which are disposed a pair of upstanding portions 6 which project from a diametral plate-like central portion 7 defined by the opposed basal surfaces 5 of the recesses 3. These upstanding portions 6 have a height measured above basal surface 5 of not more than 2 mm. Preferably the height of upstanding portions 6 measured above the basal surface 3 is from about 0.75 mm to about 1.75 mm. The upstanding portions 6 have the form of an arch in the shape of an inverted V. The overall horizontal dimension of each upstanding portion as measured on the basal surface 5 is approximately 2 mm×2 mm.

The test implant is intended for implantation into a bone of a test animal for example into a rabbit's femur, and for monitoring, in particular, the apposition of bone to the surface and amount of bone ingrowth (osteointegration) that occurs through the arches of the upstanding portions 6 in the recess 3 on one side compared to the amount occurring through the arches of the upstanding portions 6 in the recess 3 on the obverse side. In one test, the upstanding portions 6 of one recess 3 will be coated with no coating or with a different coating material from that used for the upstanding portions 6 of the other recess 3. One of these coatings can, for example, be a standard hydroxyapatite coating while the other coating material can be a test coating to be evaluated in vivo. Since the coatings are tested under effectively identical conditions in the same animal the effects of the two coatings upon the amount of osteointegration that occurs can be directly related to each other. In this way the number of animals required for use in in vivo tests can be reduced from standard methods which involve implantation of implants with different materials and coatings into different animals. Thus the use of the implant 1 enables the proper statistical evaluation of the test coating to be conducted with fewer animals.

To make the implant of FIGS. 1 and 2, a plate having the shape of the diametral portion 7 is prepared. Then the remainder of the structure is laid using selective laser melting. The test implant 11 of FIGS. 3 and 4 is generally similar to that of FIGS. 1 and 2 and has an external surface 12 that forms part of a generally cylindrical envelope, as well as recesses 13 which are substantially rectangular in shape and are surrounded by walls 14. Each recess 13 has a basal surface 15, on which are disposed a pair of upstanding portions 16 which project from a diametral plate-like central portion 17 defined by the opposed basal surfaces 15 of the recesses 13. As with upstanding portions 6, these upstanding portions 16 have a height measured above the corresponding basal surface of not more than about 2 mm, typically from about 0.75 mm to about 1.5 mm. The upstanding portions 16 each have the form of a truncated tetragonal pyramid with a pair of intersecting passages of substantially triangular cross-section through it so as to form a tetrad structure. Implant 11 can be made by any of the same techniques as are described above for the manufacture of implant 1. It can be used in a similar manner to that described for implant 1.

FIG. 5 shows a side view of a femoral implant 21 for surgical implantation during a hip replacement operation. This includes a tapered stem 22 from whose upper end there projects laterally a wedge-spaced portion 23. A ball head (not shown) for engagement with an acetabulum implanted in the patient's pelvic bone can be fitted on a frustoconical spigot 24. A bore 25 in the upper end of the stem 22 facilitates removal of the femoral implant 21 in case a revision operation is necessary.

Each of the lateral faces of wedge-shaped portion 23 is provided with a recess 26 which has a basal surface 27 on which is formed an array including a multiplicity of upstanding portions 28 in the form of tetrapod structures similar in shape to that of upstanding portions 16 of the implant of FIGS. 3 and 4. In this arrangement, the elements do not include the rim.

As can also be seen from FIG. 6, stem 22 is provided towards its upper end with similar recesses 29 and 30 in which are positioned further upstanding portions 28 which project above corresponding basal surfaces 31 and 32.

Reference numeral 33 indicates an axial recess in the top of stem 22 into which bore 25 extends.

The upstanding portions 28 can be formed on tile-like portions which are then screwed, bolted, cemented or otherwise secured to the femoral implant 21. Alternatively the entire implant 21 can be manufactured by one of the procedures described above in relation to the manufacture of implant 1.

Figure 8:
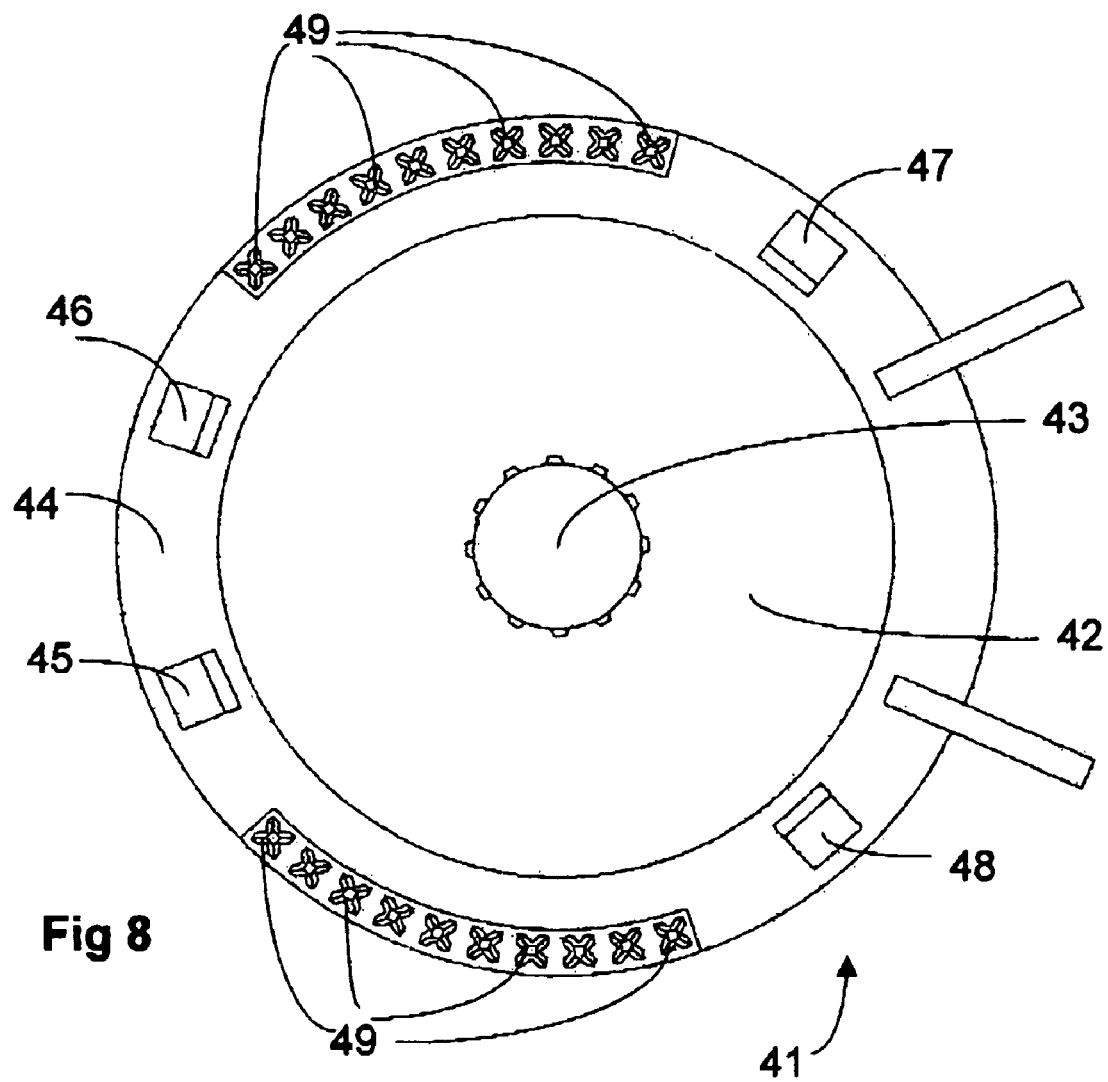
FIG. 8 is a view of the back side of an acetabular implant for implantation in a pelvic bone of a patient.

FIG. 8 shows a view from the back side of an acetabular implant 41, that is to say from the side of the implant which, after implantation, contacts the patient's pelvic bone. It comprises a substantially part-spherical body portion 42 whose convex outer surface is visible in FIG. 8. In its opposite top side there is a substantially part-spherical recess (which is not visible in FIG. 8) with a highly polished surface for reception of a ball head of a femoral implant. A stem 43 projects from a polar region of the body portion 42 for receipt in a surgically prepared bore in the pelvic bone of a patient into which the acetabular implant 41 is to be implanted. Surrounding body portion 42 is a rim portion 44 in which are formed a number of apertures 45, 46, 47, and 48 for receipt of bone screws for securing the acetabular implant in the patient's pelvic bone. On the rear face of the rim portion 44, i.e. the face which will, in use, contact the patient's pelvic bone, there are provided a plurality of upstanding portions 49 which are similar in shape to upstanding portions 16 of the implant 11 of FIGS. 3 and 4 and have a similar purpose, namely to permit bone ingrowth through the transverse passages through the tetrapod structure.

The convex underside of body portion 42, as well as the underside of rim portion 44 and the upstanding portions 49 can, if desired, be coated with a bone-compatible material such as hydroxyapatite.

The acetabular implant 41 cam be manufactured by one of the methods described for making the implants 1 and 11. Alternatively the upstanding portions 49 can be provided upon separate tile-like portions which are screwed, bolted, cemented, or otherwise secured to the acetabular implant 41.6

The invention claimed is:

1. A process for forming an element for a prosthetic implant having a bone-contacting portion provided with a plurality of upstanding portions each surrounded by a corresponding rim, wherein the upper surfaces of the upstanding portions and the rims together define an outer envelope for at least a part of the bone-contacting portion of the prosthetic implant, and wherein a basal surface comprises valleys each within a corresponding rim, said element forming a bone-contacting portion of said prosthetic implant, the element comprising a rear face, a front face, and a body extending between the rear face and the front face, wherein the front face comprises the basal surface and at least one upstanding portion projecting above the basal surface and having at least one transverse hole extending therethrough from a first side of the upstanding portion to a second side of the upstanding portion, said process comprising the steps of:
    (i) spreading a layer of metal powder on said basal surface of the front face of the element;
    (ii) selectively directing a laser to fuse the metal powder in a desired pattern to form a metallic layer overlying the basal surface of the front face; and
    (iii) repeating steps (i) and (ii) as required to build up metallic layers to form the upstanding portion of the front face projecting above the basal surface having at least one transverse hole extending therethrough.

2. A prosthetic implant having a body and at least one element made according to the process of claim 1 connected at the rear face to the body.

3. A prosthetic implant according to claim 2, wherein the at least one element is integrally formed on the surface of the prosthetic implant.

4. A prosthetic implant according to claim 3 wherein the element is integrally formed on the implant by selective laser melting.

5. A prosthetic implant according to claim 2, wherein the element is made from stainless steel, cobalt-chrome, or titanium.

6. A prosthetic implant according to claim 2, wherein the bone-contacting portion is provided with a plurality of upstanding portions each surrounded by a corresponding rim, wherein the upper surfaces of the upstanding portions and the rims together define an outer envelope for at least a part of the bone-contacting portion of the prosthetic implant, and wherein the basal surfaces comprises valleys each within a corresponding rim.

7. A prosthetic implant according to claim 2, wherein the prosthetic implant is a femoral implant, and wherein the bone-contacting portion of the prosthetic implant comprises a stem of the implant for insertion in a surgically prepared channel in a resected upper end of a femur of the patient.

8. A prosthetic implant according to claims 2, wherein the prosthetic implant is a femoral implant having a stem for insertion in a surgically prepared channel in a resected upper end of a femur of the patient, and a wedge-shaped portion having a front face and a rear face extending laterally from an upper end of the stem and a spigot for receipt of ball head, the ball head being adapted for insertion in a natural or artificial acetabular socket, and wherein the bone-contacting portion of the prosthetic implant comprises at least a portion of at least one out of the front and rear faces of the wedge-shaped portion.

9. A prosthetic implant according to claim 2, wherein the prosthetic implant is a femoral implant having a stem for insertion in a surgically prepared channel in a resected upper end of a femur of the patient, a wedge-shaped portion having a front face and a rear face extending laterally from an upper end of the stem, and a ball head on the wedge-shaped portion, the ball head being adapted for insertion in a natural or artificial acetabular socket, and wherein the bone-contacting portion of the prosthetic implant comprises at least a portion of at least one out of the front and rear faces of the wedge-shaped portion.

10. A process according to claim 9, wherein the upstanding portion above the basal surface has a height of less than about 2 mm.

11. A process according to claim 10, wherein the height of the upstanding portion above the basal surface is from about 0.75 to about 1.75 mm.

12. A process according to claim 9, wherein at least one transverse hole has an axis extending substantially parallel to the basal.

13. A process according to claim 9, wherein at least one upstanding portion has of an arched configuration.

14. A process according to claim 9, wherein at least one upstanding portion substantially comprises a truncated pyramid.

15. A process according to claim 14, wherein the truncated pyramid is a truncated rectangular pyramid, a truncated square pyramid, a truncated triangular pyramid or a truncated hexagonal pyramid.

16. A process according to claim 15, wherein the upstanding portion is a truncated rectangular or square pyramid provided having first and second holes each of which extends from a first face to a second face opposite the corresponding first face.

17. A process according to claim 16, wherein the two holes intersect substantially at right angles.

18. A process according to claim 15, wherein the upstanding portion comprises a truncated triangular pyramid and has a first hole extending from a first face, being in the interior of the upstanding portion, and extending to a second face of the upstanding portion, and wherein the upstanding portion is provided with a second hole extending from a third face and intersecting the first hole.

19. A process according to claim 14, wherein the upstanding portion comprises a truncated hexagonal pyramid and has first, second and third holes, each hole extending from a first face to a second face opposite the corresponding first face.

20. A process according to claim 19, wherein the first, second and third holes all intersect each other.

21. A process according to claim 1, wherein the basal surface is surrounded by a raised rim.

22. A process according to claim 1, wherein the element is substantially rectangular in plan.

23. A process according to claim 1, wherein the basal surface is substantially rectangular.

24. A process according to claim 23, wherein the basal surface has a dimension of about 2 mm by about 4 mm.

25. A process according to claim 1, wherein the element has the form of a sleeve and wherein the rear face comprises the inner face of the sleeve and the front face comprises the outer face of the sleeve.

26. A process according to claim 1, wherein the element is formed from stainless steel, cobalt-chrome or titanium.

27. A process according to claim 1, wherein the metal powder has a particle size of about 20 μm.

28. A process according to claim 27, including directing the laser as required to produce bridges.

* * * * *